United States Patent [19]

Liburdy

[11] 4,411,789
[45] Oct. 25, 1983

[54] MAGNETIC RESONANCE CHROMATOGRAPHY

[76] Inventor: Robert P. Liburdy, 1245 Park Ave., Apt. 16A, New York, N.Y. 10028

[21] Appl. No.: 295,035

[22] Filed: Aug. 21, 1981

[51] Int. Cl.³ .................................................. B01D 15/08
[52] U.S. Cl. .................................. 210/635; 210/695; 210/198.2; 210/223
[58] Field of Search ........ 210/635, 656, 695, 198.2, 210/223

[56] References Cited

U.S. PATENT DOCUMENTS

| | | | |
|---|---|---|---|
| 3,002,823 | 10/1961 | Flodin et al. | 23/293 |
| 3,719,583 | 3/1973 | Ustick | 210/695 X |
| 4,238,327 | 12/1980 | Liburdy | 210/656 |
| 4,314,905 | 2/1982 | Etzel et al. | 210/223 X |

OTHER PUBLICATIONS

"Development and Construction of an Electromagnetic Near-Field Synthesizer", National Bureau of Standards, NBS Technical Note 652, May 1974.

*Primary Examiner*—John Adee
*Attorney, Agent, or Firm*—Donald J. Singer; Jacob N. Erlich

[57] ABSTRACT

A magnetic resonance chromatography system that enables the separation of charge carrying molecules to effectively take place. An oscillating magnetic field is generated in free space and applied in one of numerable orientations with the field lines parallel to the longitudinal axis of a chromatography column containing the gel media of a liquid gel chromatography apparatus. Molecules within the gel media which posses either a net positive or negative charge experience an "induced" flow due to eddy currents produced in the chromatography column. These "induced" flow events alter the motion of the charged molecules and therefore effect molecule separation.

6 Claims, 5 Drawing Figures

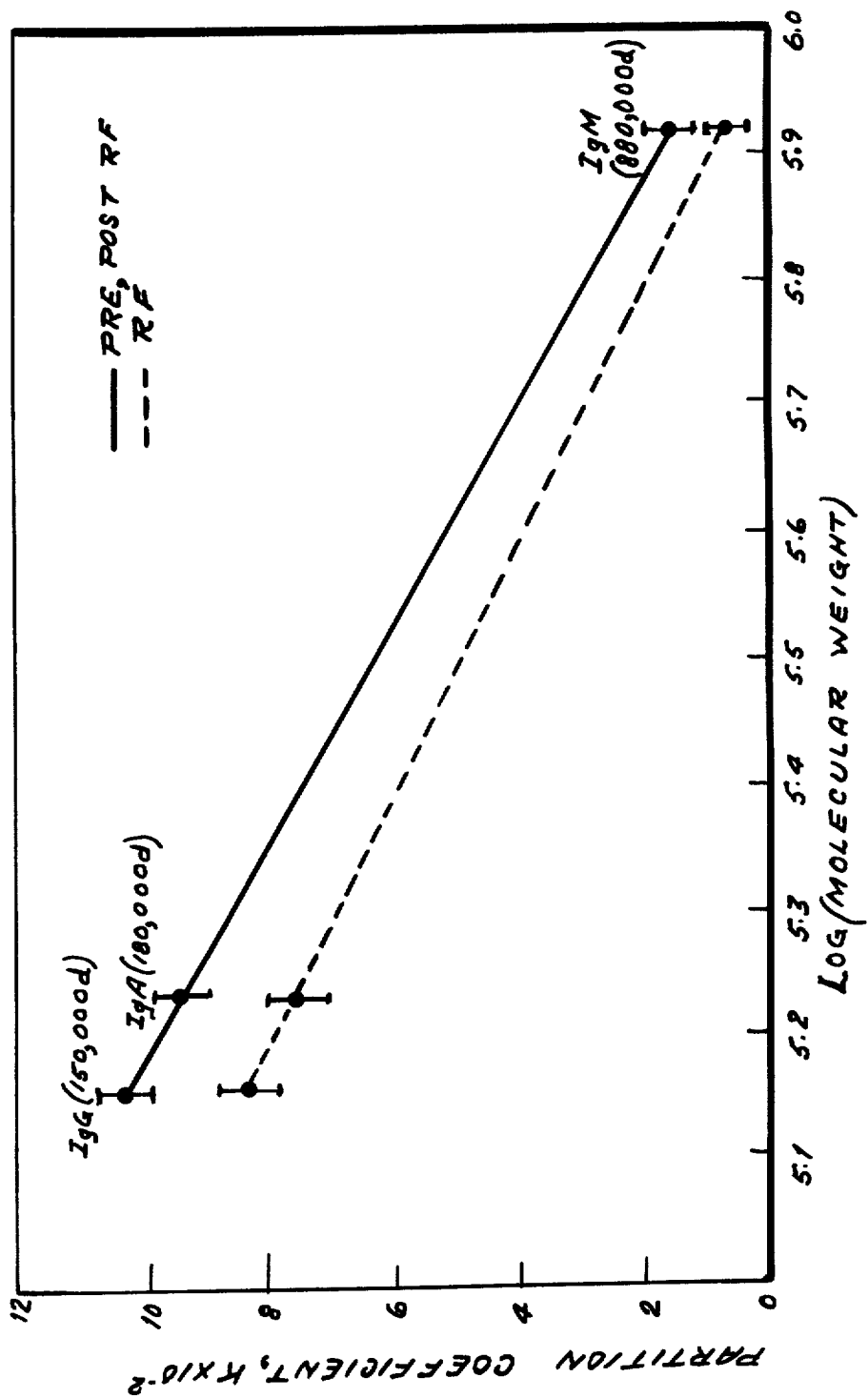

MAGNETIC RESONANCE CHROMATOGRAPHY

STATEMENT OF GOVERNMENT INTEREST

The invention described herein may be manufactured and used by or for the Government for governmental purposes without the payment of any royalty thereon.

BACKGROUND OF THE INVENTION

This invention relates generally to the field of liquid gel chromatography, and, more particularly to a magnetic resonance chromatography system that separates molecules such as cells and proteins into different populations based upon their interactions with a magnetic field oscillating at radio frequencies.

Liquid gel chromatography (LGC) is an established laboratory technique for the differential fractionation and separation of molecules. The underlying premise for simple LGC is that molecules elute from a gel bed in order of decreasing molecular weight. Generally, gel particles fill a chromatography column to form a bed. When the molecules to be partitioned, such as cells or proteins are introduced and driven through the bed by supplemental eluent, the molecules separate on the basis of molecular weight. That is, the larger molecules separate and elute first. Thus, the elution order is one of decending size. Since liquid gel chromatography in general and gel permeation type LGC in particular, are well known by those practicing in the related arts, and are adequately described in references such as U.S. Pat. No. 3,002,823 to P. G. M. Flodin et al further elaboration is superfluous.

Though a multitude of refinements have been developed to improve the distinctness of the partitioning and increase its rate, better resolution of molecular species on the basis of weight and shape continues to be sought. This is particularly true when complex cell or protein populations, such as biological fluids are being separated. In such cases, the conventional approaches involve successive LGC filtration steps or the concurrent use of other perturbation techniques to alter the environment during the LGC process. For example, detergents and salts have been used to provide unique environmental effects.

Electric resonance chromatography (ERC) as described in the inventor's U.S. Pat. No. 4,238,327 issued Dec. 9, 1980 is a recent example of a new refinement in LGC molecular separation utilizing an applied electric field for a unique effect. In this refinement conventional LGC is improved so that ERC can both accelerate separation and accentuate the ability to distinctly identify molecular groups within the population that possess an electric dipole moment (that is, charge separation) and, thus, interact with the applied electric field. In gel filtration terms, the elution time is decreased for these species while the zones are narrowed.

Although the above known techniques have been used successfully in most instances, in the ever expanding field of chromatography there always exists a need for alternative systems to separate molecules. For example, there exist proteins and cells that do not possess a net electric dipole (charge separation) moment even though they possess charged groups. These species will not interact with an applied electric field as described in U.S. Pat. No. 4,238,327 referred to above. Therefore, by the development of further and other techniques more efficient and reliable separation would be attainable.

SUMMARY OF THE INVENTION

The magnetic resonance chromatography (MRC) system of this invention overcomes the problems encountered in the past by providing a chromatography procedure that separates charge carrying molecules such as cells and proteins into different populations based upon their interactions with a magnetic field oscillating at radio frequencies (RF) wherein radio frequency is defined as any frequency between 10 Mhz and 100 GHz although, in principle, any oscillating magnetic field will produce the desired effect. More specifically, the MCR system of this invention is capable of facilitating the separation of molecules possessing a net positive or negative charge which do not possess a electric dipole moment and therefore cannot be effectively separated by prior techniques.

The magnetic resonance chromatography system of this invention came about as a result of the inventor's discovery that such charged species will undergo an "induced" flow in the direction of an eddy current that is established by an oscillating magnetic field. With the technique of the present invention an RF magnetic field generator is utilized in conjunction with a liquid gel chromatography column and automated monitor. The oscillating magnetic field is generated in free space and applied with the field lines, in the present application, parallel to the longitudinal axis of the chromatography column. Other orientations for the magnetic field lines are possible and will affect only the geometry of the field with the direction of the column flow.

Molecules that possess a net charge when in the presence of the oscillating magnetic field experience an "induced" flow due to eddy currents produced in the chromatography column. These "induced" flow events alter the motion of the charged molecules or species and affect the process and separation in the column. This induced effect is the major basis for new separation patterns and applies to proteins and cells that possess a net charge.

A second effect that occurs is one involving orientation with the applied magnetic field due to the presence of magnetic dipoles (magnetic polarization). This effect is most likely not as significant as the "induced" flow due to eddy currents, but will be present for species that are diamagnetic, paramagnetic, or ferromagnetic in nature.

The effects produced by this invention are frequency dependent and therefore particular cells or proteins are influenced by magnetic fields oscillating at frequencies corresponding to lateral diffusion and rotational relaxation times for the species. As a result the separation process for molecules is dependent upon the interaction between the proteins and cells and the magnetic field.

It is therefore an object of this invention to provide a magnetic resonance chromatography system which enables the separation of cells and proteins into distinct populations that have unique change and magnetic polarization during hydrodynamic sieving in LGC.

It is another object of this invention to provide a magnetic resonance chromatography system which makes possible the isolation, purification, and identification of species for both analytical and preparative purposes.

It is a further object of this invention to provide a magnetic resonance chromatography system which can have a wide range of applicability, as for example, in industrial, clinical and research activities.

It is still another object of this invention to provide a magnetic resonance chromatography system which is economical and which utilizes conventional, currently available components therein.

For a better understanding of the present invention, together with other and further objects thereof, reference is made to the following description taken in conjunction with the accompanying drawing and its scope will be pointed out in the appended claims.

DETAILED DESCRIPTION OF THE DRAWING

Figure 4:
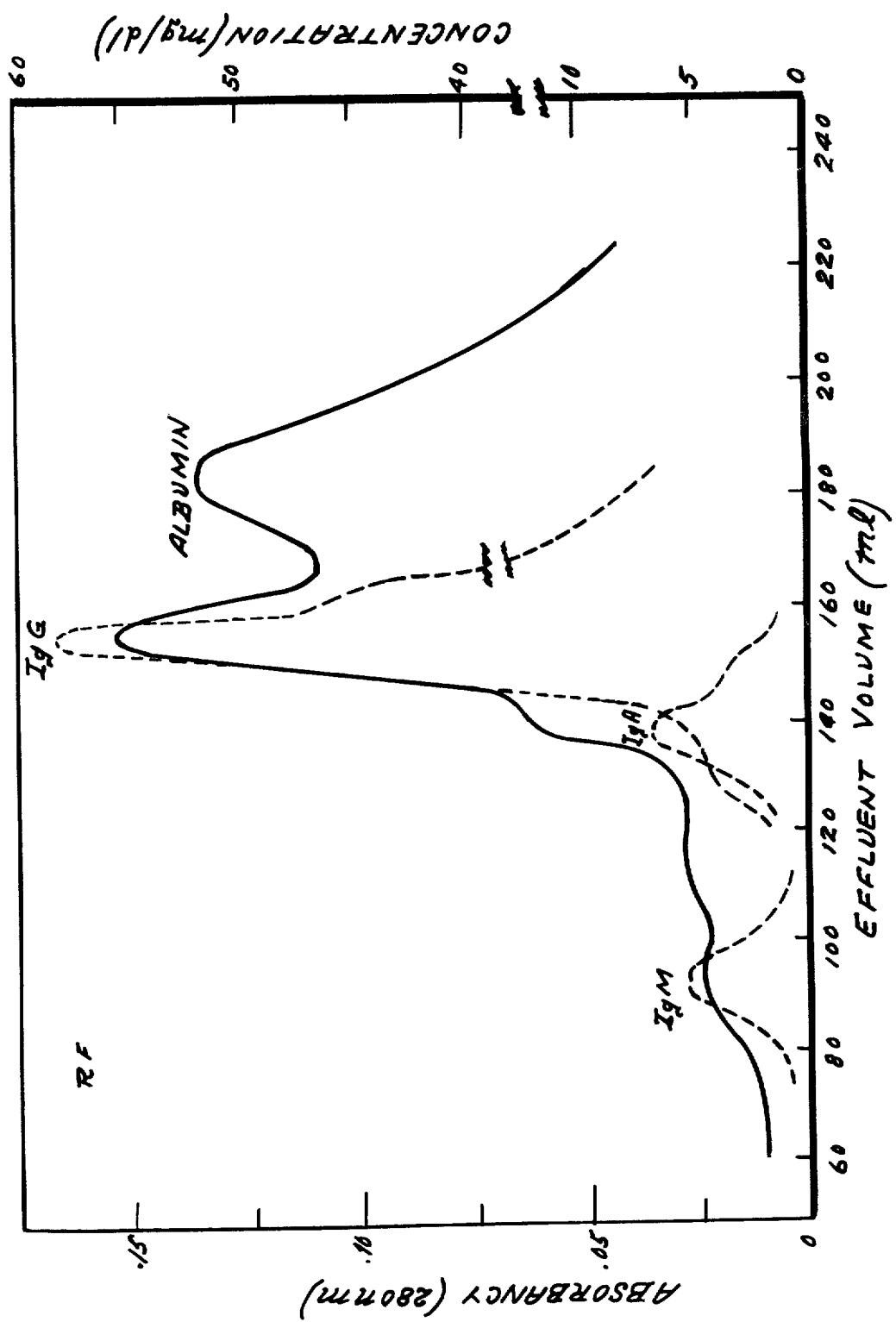

FIG. 4 is a graphic representation of the data obtained for human serum separated over the column during exposure to the RF magnetic field during the magnetic resonance chromatography procedure of this invention; and FIG. 5 is a graphic representation of quantitatively analyzed data having the partition coefficient plotted versus the log of the proteins after having undergone RF magnetic field exposure by the magnetic resonance chromatography procedure of this invention.

DETAILED DESCRIPTION OF THE PREFERRED EMBODIMENT AND METHOD

Figure 1:
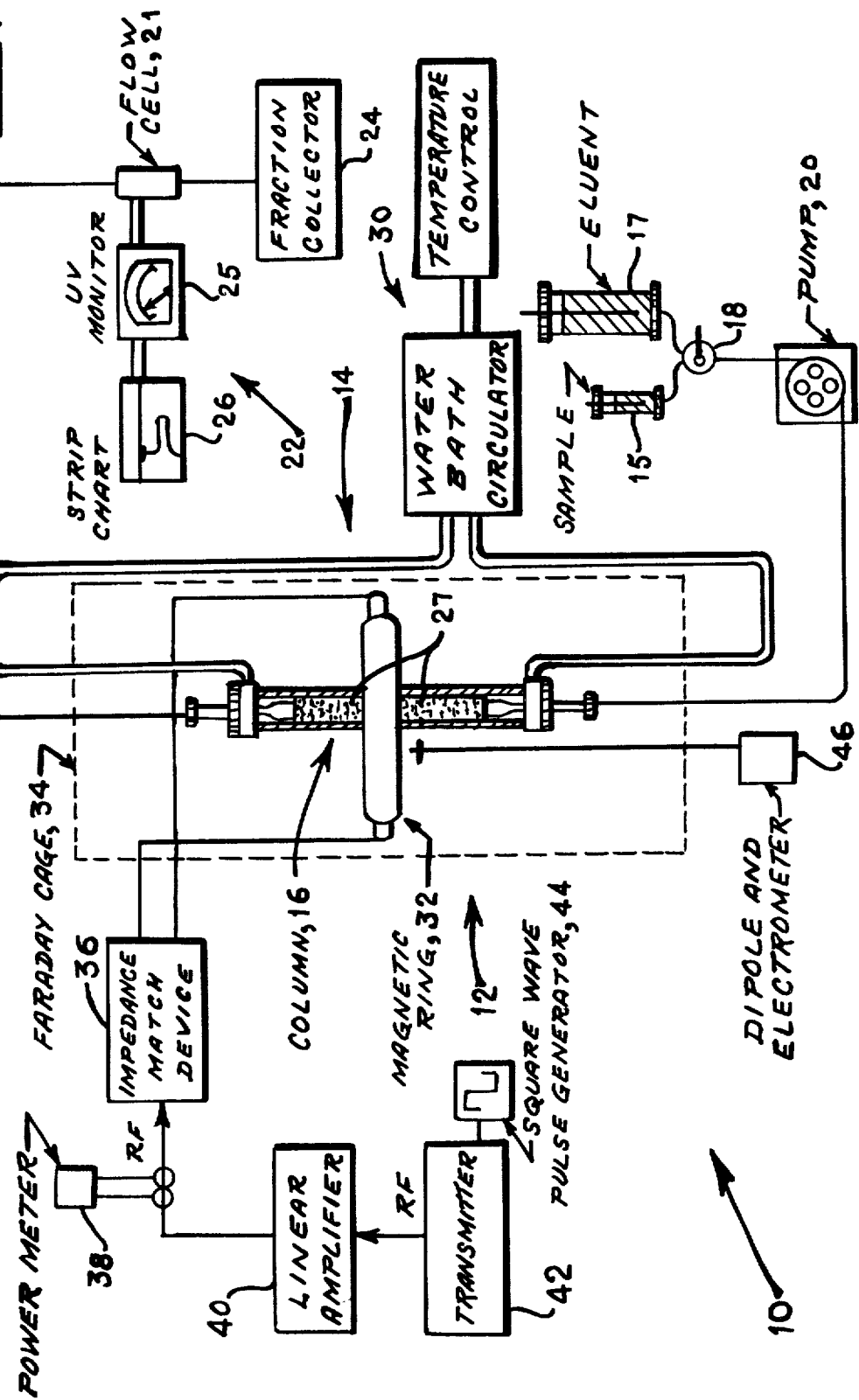
FIG. 1 is a side elevational view shown partly in schematic fashion of the apparatus used as part of the magnetic resonance chromatography system of this invention.

Reference is now made to FIG. 1 of the drawing which clearly depicts the apparatus 10 making up the magnetic resonance chromatography system of this invention. Apparatus 10 incorporates therein two main components, an RF magnetic field generator 12 and a conventional gel permeation type liquid gel chromatography structure 14 which in this case utilizes an ascending chromatography column 16. Since the LGC apparatus 14 is well known and commerically available from, for example, Pharmacia Fine Chemicals (Piscataway, N.J.) and Instruments Specialties Company (Lincoln, Nebr.) its operation need not be described with particularity.

Figure 2:
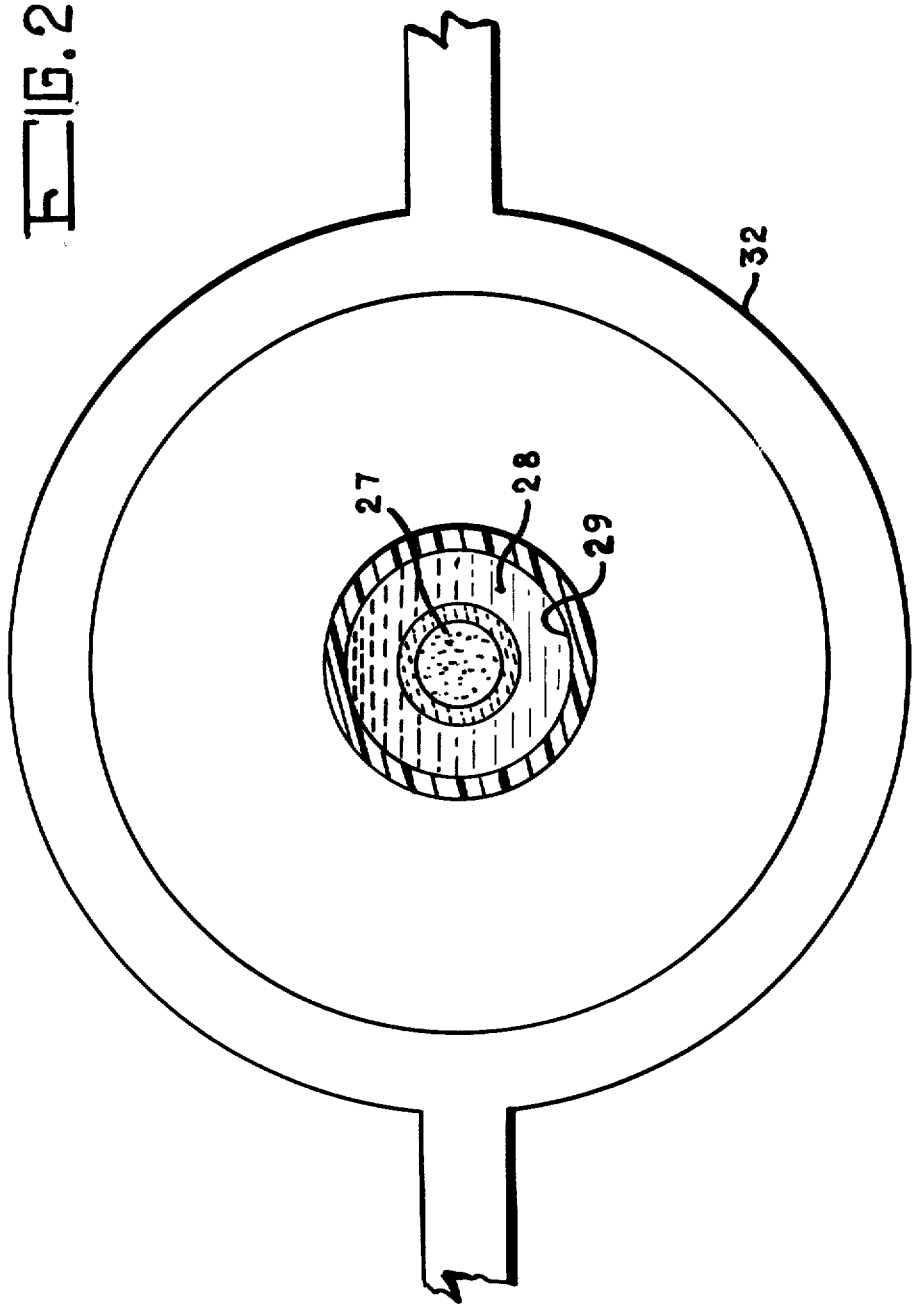
FIG. 2 is a plan view of the chromatography column utilized in conjunction with the magnetic field generator of the magnetic resonance chromatography system of this invention and shown partly in cross section.

In general, however, a sample material 15 and eluent 17 are selectively regulated by a valve 18 and then driven through column 16 by a peristaltic pump 20. Valve 18 has three positions; a position in which both sample 15 and eluent 17 are off, a position in which only the sample 15 passes, and a position in which only eluent 17 passes. The output from column 16 is directed through flow cell 21 forming part of a detector unit 22 and then enters a fraction collector 24. Within detector unit 22 a UV monitor 25 responds to variations in absorbancy of the material passing through flow cell 21 and permanently records these signals on a strip chart recorder 26. Column 16, and the materials 27 passing therethrough, are maintained at a substantially constant temperature by the circulation of distilled water 28 at approximately 25° C. through its outer jacket 29 more clearly depicted in FIG. 2 of the drawing. Circulation of distilled water 28 takes place by means of water bath circulator and temperature control 30.

More specifically a typical sample 15 contains human serum which is comprised of numerous protein constituents. Human serum, for example, contains three important immunoglobulins, IgG, IgA, and IgM, which can be separated by liquid gel chromatography. A typical eluent 17 which may be used with this invention is commonly known as phosphate buffered saline, with a pH of 6.96 at 25° C., formed from 0.9% W/V saline in glass distilled $H_2O$ to which is added 0.05 M phosphate buffer.

Column 16 may be, for example, a model K-26 chromatography column manufactured by Pharmacia Fine Chemicals (Piscataway, N.J.), while reference numerals 21, 24, 25 and 26 designate pieces of automated monitor-collector equipment from Instrument Specialties Company (Lincoln, Nebr.). A gel media which can be utilized with this particular embodiment, can be Sephadex G-200 (superfine), although other gel media such as Sephadex G-100 and Sephacryl G-200 are also readily acceptable. All three gel media are trademark products manufactured by Pharmacia Fine Chemicals.

Since the control of the material admitted into pump 20 by valve 18 conformed to the manufacturer's instructions when using the gel media and column 16 it need only be noted that the following illustrative example uses 1-2 mg of the mixture in the sample to create the response described and plotted hereinbelow. Procedurally, valve 18 is first set to fill column 16 with eluent 17. Once column 16 is filled, valve 18 is set to allow sample 15 to flow until 1-2 mg are introduced. Thereafter, valve 18 is returned to its eluent flow position. Eluent flow is maintained until column 16 is cleared of sample material.

Reference is now made specifically to the RF magnetic field generator 12 an essential part of this invention. RF magnetic field generator 12 is made up of the following elements: magnetic ring 32 encompassing column 16, Faraday cage 34, an impedance matching device 36, a power meter 38, a linear amplifier 40, an RF transmitter 42, a square wave pulse generator 44 and a dipole and electrometer 46, all of which are more specifically described with reference to the RF magnetic field generator referred to in the National Bureau of Standards (NBS) technical note 652, issued in May 1974 and entitled "Development and Construction of an Electromagnetic Near-Field Synthesizer". It is noted that the RF magnetic field generator 12 of this invention is designed to generate a pure magnetic field oscillating at RF frequencies without any electric field component, whatsoever.

MODE OF OPERATION

More specifically, the magnetic resonance chromatography (MRC) system of this invention is a chromatography separation process based upon a new "induced" cell or protein flow during liquid gel chromatography, and a magnetic field orientation for species that are diamagnetic, paramagnetic, or ferromagnetic. The latter effect is probably secondary and may be significantly reduced compared to the "induced" flow due to eddy currents.

Application of an external magnetic field by means of magnetic ring 32 during liquid gel chromatography results in an "induced" flow and a magnetic polarization of cells or proteins within the chromatography column 16 to change their flow patterns through the chromatography media. Cells or proteins with a net positive or negative charge will take on a new "induced" flow in the direction of eddy currents established by the oscillating magnetic field which, in this application, runs parallel to the longitudinal axis of the chromatography column 16.

With a set up as depicted in FIG. 1 of the drawing, the eddy currents will be established so as to move clockwise and then counterclockwise in a plane parallel to the plane of the magnetic ring as the magnetic field changes direction or oscillates. The proteins or cells being separated which carry a net charge will be acted upon by the eddy currents in order to undergo a change in flow to coincide with the direction of the eddy currents. This imparts a special "induced" flow to the proteins and cells. Species that are diamagnetic, paramagnetic, or ferromagnetic will experience a magnetic polarization and align with the magnetic field lines.

The induced flow and the polarization effects involves a rotational motion so that the magnetic dipole and applied field coincide. The time course for lateral diffusion and rotational diffusion is on the order of $10^{-6}$ seconds for relatively large proteins, but it is shorter for smaller structures such as polar amino acid side chains and water molecules bound to the surface of cells. Thus, by varying the oscillating frequency of the applied magnetic field different molecular structures can be influenced. In a sense column 16 can be tuned to a frequency that is resonant for a particular species, hence magnetic resonance chromatography.

Figure 3:
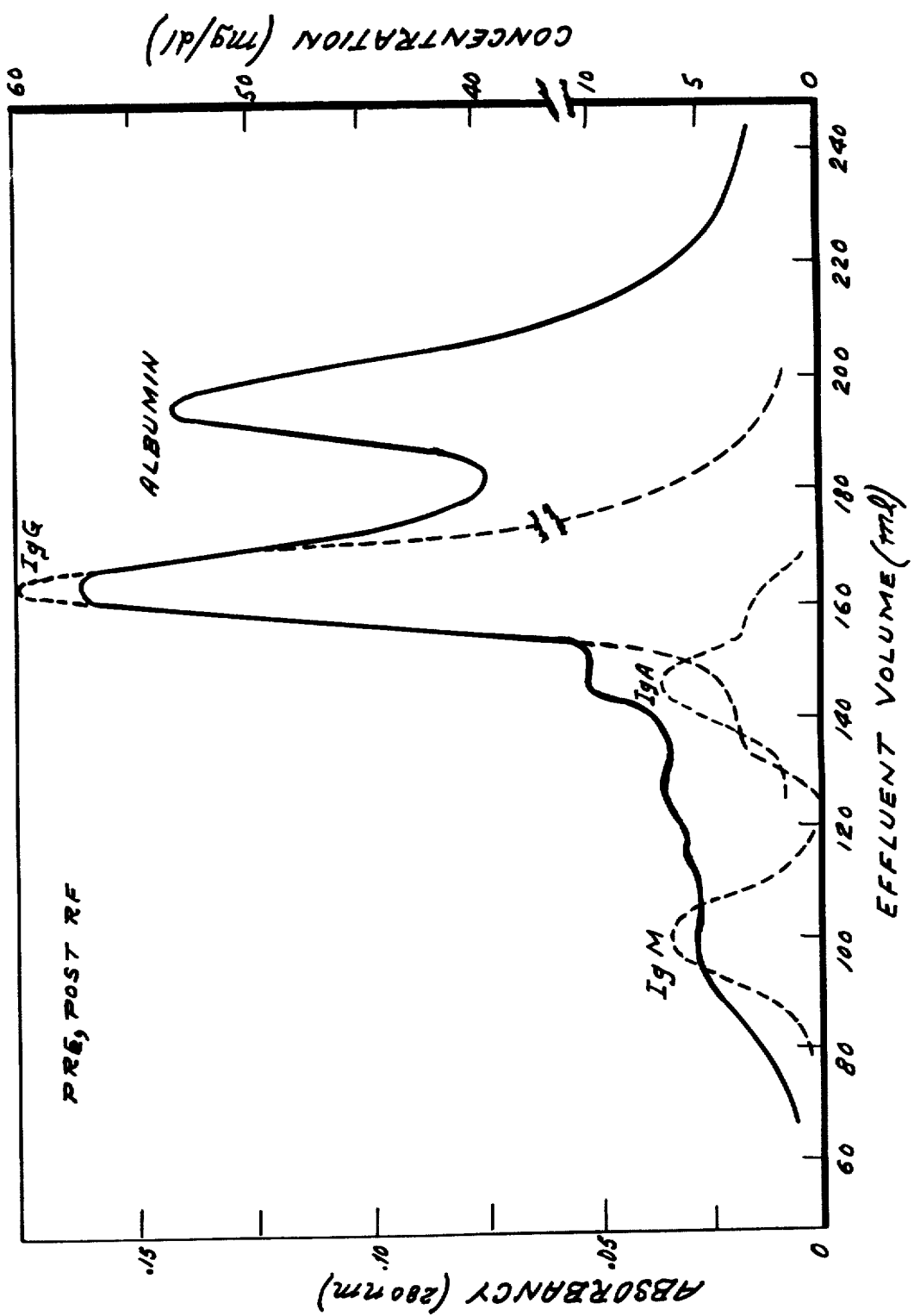
FIG. 3 is a graphic representation of a typical elution profile for human serum.

At the molecular level the ordinary, standard chromatography process operates to separate species by size, or hydrodynamic cross-section. Large molecules pass through a matrix of polymer branches called dextran, that make up a system of interconnecting pores. Smaller molecules take considerably longer time to pass through a matrix because they penetrate a greater number of smaller pores, and they are separated from the larger molecules. Thus larger species flow off column 16 first followed by increasingly smaller species. FIG. 3 of the drawing illustrates in graphic form a typical elution profile for human serum. Human serum is a complex mixture of many proteins and identified here are three of interest: immunoglobulin M, IgM; immunoglobulin A, IgA; immunoglobulin G, IgG. The peaks corresponding to each protein is shown in a dashed line, and were identified by radial immunodiffusion techniques. The data in FIG. 3 was obtained before and after exposure of column 16 to RF magnetic fields and note that there is no difference between the data, that is, they superimpose.

The graph of FIG. 4 shows the data obtained for human serum separated over column 16 during exposure to the RF magnetic field. Note that comparison with the data in FIG. 3 reveals that each protein species flowed off the column in less volume. The interpretation is that the magnetic field caused the protein to appear larger; that is the "induced" flow and magnetic field orientation increased the cross-section and the molecules took on a larger "apparent" volume. This accounts for the rapid elution in the presence of the RF magnetic field.

This data can be analyzed quantitatively by plotting the partition coefficient, K, against the log (molecular weight) of the protein. This is shown in the graph of FIG. 5, where K is given as the ratio $(V_e - V_o)/(V_t - V_o)$ where $V_e$ = the elution volume for the protein, $V_o$ = the void volume for the packed column, and $V_t$ = the total volume for the packed column. Notice that the case for RF magnetic field exposure resulted in reduced values for K. This means that the proteins partitioned to a lesser degree as would be expected for larger proteins.

It is therefore readily apparent after an understanding of the above disclosure that the Magnetic Resonance Chromatography system of this invention can selectively separate populations of cells or proteins which possess a net charge and/or a magnetic dipole by exposing the species to an oscillating magnetic field. The frequency of choice depends on the species lateral diffusion and rotational relaxation.

Although this invention has been described with reference to a particular embodiment it will be understood to those skilled in the art that this invention is also capable of a variety of alternative embodiments within the spirit and scope of the appended claims.

I claim:

1. In a liquid gel chromatography apparatus having a gel media for partitioning molecules possessing a net positive or negative charge, the improvement therein comprising means operably associated with said chromatography apparatus for generating an oscillating magnetic field which produces eddy currents within said gel media, whereby said eddy currents effect separation patterns for said molecules.

2. In a liquid gel chromatography apparatus as defined in claim 1 wherein said chromatography apparatus include a chromatography column for containing said gel media and said magnetic field is generated in free space and applied with the field lines substantially parallel to the longitudinal axis to said chromatography column.

3. In a liquid gel chromatography apparatus as defined in claim 1 wherein said magnetic field oscillates at preselected frequencies and said molecules are influenced by said frequencies corresponding to lateral diffusion and rotational relaxation times for said molecules.

4. A method for enhancing the partitioning of molecules possessing a net positive or negative charge comprising the steps of:
    (a) containing said molecules within a gel media within a liquid gel chromatography apparatus; and
    (b) applying an oscillating magnetic field to said gel media thereby producing eddy currents within said gel media
    whereby said molecules experience an "induced" flow due to said eddy currents and therefore establish new separation patterns.

5. A method for enhancing the partitioning of molecules possessing a net positive or negative charge as defined in claim 4 further comprising the steps of containing said gel media within a chromatography column included as part of said chromatography apparatus and applying said magnetic field to said gel media with the field lines of said magnetic field substantially parallel to the longitudinal axis of said chromatography column.

6. A method for enhancing the partitioning of molecules possessing a net positive or negative charge as defined in claim 4 further comprising the step of oscillating said magnetic field at preselected frequencies whereby said molecules are influenced by said frequencies corresponding to lateral diffusion and rotational relaxation times for said molecules.

* * * * *